United States Patent [19]

Schulz

[11] 4,334,084

[45] Jun. 8, 1982

[54] ORGANIC ACIDS AND PROCESS FOR PREPARING SAME

[75] Inventor: Johann G. D. Schulz, Pittsburgh, Pa.

[73] Assignee: Gulf Research & Development Company, Pittsburgh, Pa.

[21] Appl. No.: 910,215

[22] Filed: May 30, 1978

[51] Int. Cl.³ .................... C07C 51/373; C07C 51/47
[52] U.S. Cl. .................................. 562/410; 562/485; 562/407
[58] Field of Search .......... 260/515 H, 515 M, 515 P, 260/524 N; 562/410, 485, 407

[56] References Cited

U.S. PATENT DOCUMENTS 4,052,448  10/1977  Schulz et al. ................... 260/515 H

OTHER PUBLICATIONS

Polansky, Theodore S. et al., "Solvent Extraction of Humic Acids from Nitric Acid-Treated Bituminous Coal", Ind. & Eng. Chemistry, 39, (7), 926-929, (1947).

Fuchs, Walter et al., "Coal Oxidation", Industrial and Engineering Chemistry, vol. 35, pp. 343-345, (1943).

Bease, A. E. et al., "Production of Chemicals by Oxidation of Coal", A Batelle Energy Program Report, Mar. 31, 1975, (Batelle Memorial Institute, Columbus, Ohio).

Kinney, C. R. et al., "Nitric Acid Oxidation of Bituminous Coal", Industrial and Engineering Chemistry, vol. 48, pp. 327-332, (1956).

Kirk-Othmer, "Encyclopedia of Chemical Technology, vol. I, pp. 92-95, (1950), Interscience Publ.

*Primary Examiner*—Natalie Trousof
*Assistant Examiner*—L. Hendriksen
*Attorney, Agent, or Firm*—Deane E. Keith; Forrest D. Stine; Joseph J. Carducci

[57] ABSTRACT

A mixture of polycyclic, aromatic polycarboxylic acids carrying nuclear nitro groups that is substantially soluble in a mixture of polar solvents but substantially insoluble in water and a process for preparing the mixture of polycyclic, aromatic polycarboxylic acids.

10 Claims, No Drawings

ORGANIC ACIDS AND PROCESS FOR PREPARING SAME

BACKGROUND OF THE INVENTION

1. Field of the Invention

This invention relates to a mixture of polycyclic, aromatic polycarboxylic acids carrying nuclear nitro groups that is substantially soluble in a mixture of polar solvents but substantially insoluble in water and a process for preparing the mixture of polycyclic, aromatic polycarboxylic acids.

2. Description of Prior Art

In U.S. Pat. No. 4,052,448 to J. G. Schulz and E. T. Sabourin there is disclosed a mixture of polycyclic, aromatic polycarboxylic acids carrying nuclear nitro groups that is substantially soluble in a polar solvent but substantially insoluble in water and a process for preparing the mixture.

SUMMARY OF THE INVENTION

The process defined and claimed herein is directed to an improvement in the process claimed in U.S. Pat. No. 4,052,488. I have found that if in the process of the patent a mixture of two polar solvents, one being a ketone and the other being an alcohol, is used in place of a ketone alone or an alcohol in recovering the desired mixture of polycyclic, aromatic polycarboxylic acids, an unexpectedly larger amount of polycylic, aromatic polycarboxylic acids is obtained than when only a ketone or an alcohol is used.

The individual components of the novel mixtures of polycyclic, aromatic polycarboxylic acids obtained herein are believed to be composed of condensed and/or non-condensed benzene rings, with an average number of rings in the individual molecules ranging from 2 to about 10, but generally from 3 to about 8. On the average, the number of carboxyl groups carried by the individual molecules will range from about 4 to about 10, generally from about 6 to about 8, and the average number of nitro groups from about 1 to about 4, generally from about 2 to about 3. The average molecular weight of the mixture will range from about 600 to about 1500, generally from about 700 to about 1000, and the average neutral equivalent will range from about 80 to about 200, generally from about 100 to about 150. A typical analysis of the novel mixture is defined below in Table I in approximate amounts.

TABLE I

|  | Weight Percent | |
| --- | --- | --- |
|  | Broad Range | Preferred Range |
| Carbon | 50 to 60 | 52 to 56 |
| Hydrogen | 3 to 5 | 3.7 to 4.4 |
| Nitrogen | 3 to 6 | 4 to 5 |
| Oxygen | 25 to 45 | 30 to 40 |
| Sulfur | 0.2 to 0.5 | 0.3 to 0.5 |
| Ash | 0.1 to 5.0 | 0.3 to 3.0 |

The ketone used in the mixture of solvents herein is selected from the group consisting of ketones defined by the following formula:

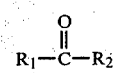

and cyclohexanone, wherein $R_1$ and $R_2$, the same or different, are alkyl groups having from one to four carbon atoms, preferably from 1 to 2 carbon atoms, such as methyl, ethyl, isopropyl, n-butyl etc. Specific examples of such ketones include acetone, methyl ethyl ketone and cyclohexanone. The alcohol used in combination with the above ketone can be defined by the following formula:

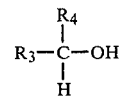

wherein $R_3$ and $R_4$, the same or different, can be hydrogen or alkyl groups having from one to four carbon atoms, preferably from 1 to 2 carbon atoms, such as methyl, ethyl, isopropyl, n-butyl, etc. Specific examples of such alcohols include methanol, ethanol and isopropanol.

The amount of each polar solvent present in the solvent mixture defined above can be varied over a wide range, but most preferably the amount of each present will be that amount just sufficient to form an azeotropic mixture when the solvent mixture is subjected to distillation at ambient pressure. Preferably, the amount of each polar solvent present is not in excess of about ten weight per cent, preferably not in excess of about five weight per cent, of that amount necessary to form the desired azeotropic mixture.

The procedure employed herein preferably follows the procedure defined in U.S. Pat. No. 4,052,448. Thus there is introduced into a reactor an aqueous solution of nitric acid and a carbonaceous material. The nitric acid can have a concentration of about 5 to about 90 percent, but preferably will be in the range of about 10 to about 70 percent. The carbonaceous material is preferably a solid in the form of a slurry, for example, an aqueous slurry containing the carbonaceous material in particulate form and from about 50 to about 90 weight percent of water.

The solid carbonaceous material that can be used herein can have the following composition on a moisture-free basis:

TABLE II

|  | Weight Percent | |
| --- | --- | --- |
|  | Broad Range | Preferred Range |
| Carbon | 45–95 | 60–92 |
| Hydrogen | 2.5–7 | 4–6 |
| Oxygen | 2.0–45 | 3–25 |
| Nitrogen | 0.75–2.5 | 0.75–2.5 |
| Sulfur | 0.3–10 | 0.5–6 |

The carbon and hydrogen content of the carbonaceous material will reside primarily in multi-ring aromatic compounds (condensed and/or uncondensed), heterocyclic compounds, etc. Oxygen and nitrogen are believed to be present primarily in chemical combination. Some of the sulfur is believed to be present in chemical combination with the aromatic compounds and some in chemical combination with inorganic elements associated therewith, for example, iron and calcium.

In addition to the above the solid carbonaceous material being treated herein will also contain solid, primarily inorganic, compounds which will not be converted to the desired organic mixture claimed herein, which are termed ash, and are composed chiefly of compounds of silicon, aluminum, iron and calcium, with smaller amounts of compounds of magnesium, titanium, sodium and potassium. The ash content of the carbonaceous material treated herein will amount to less than about 50 weight percent, based on the moisture-free carbonaceous material, but, in general, will amount to about 0.1 to about 30 weight percent, usually about 0.5 to about 20 weight percent.

Anthracitic, bituminous and subbituminous coal, lignitic materials, and other type of coal products referred to in ASTM D-388 are exemplary of the solid carbonaceous materials which can be treated in accordance with the process defined herein to produce the claimed organic mixture. Some of these carbonaceous materials in their raw state will contain relatively large amounts of water. These can be dried prior to use herein. The carbonaceous material, prior to use, is preferably ground in a suitable attrition machine, such as a hammermill, to a size such that at least about 50 percent of the carbonaceous material will pass through a 40-mesh (U.S. Series) sieve. As noted, the carbonaceous material is slurried in a suitable carrier, preferably water, prior to reaction with nitric acid. If desired, the carbonaceous material can be treated, prior to reaction herein, using any conventional means, to remove therefrom any materials forming a part thereof that will not be converted in reaction with nitric acid herein.

The reactant mixture in the reactor is stirred while being maintained at a temperature of about 15° to about 200° C., preferably about 50° to about 100° C., and a pressure of about atmospheric to about 1000 pounds per square inch gauge (about atmospheric to about 70 kilograms per square centimeter), preferably about atmospheric to about 500 pounds per square inch gauge (about atmospheric to about 35 kilograms per square centimeter) for about 0.5 to about 15 hours, preferably about two to about six hours. In order to obtain the desired mixture herein without losing appreciable amounts of carboxyl and/or nitro groups on the acids that are formed during the oxidation and to obtain the desired acids in high yields in the reactor, it is absolutely critical that the reaction conditions therein, namely nitric acid concentration, temperature, pressure and reaction time, be so correlated to minimize and, preferably, to avoid decarboxylation and denitrofication. Gaseous products, such as nitrogen oxides, can be removed from the reactor as they are formed.

The reaction product is removed from the reactor upon completion of the reaction. The reaction product is soluble in, or reactable with, sodium hydroxide. At this point it is necessary to separate the oxidized product from the water and nitric acid associated therewith. This separation must be accomplished in a manner so that the carboxyl and nitro groups are not removed from the acid product. Distillation for the removal of water will not suffice, because under the conditions required for such separation, a significant loss of carboxyl groups and nitro groups would occur. Accordingly, it has been found that a mechanical separation will suffice. The reaction product is therefore led to a first separator which can be, for example, a filter or a centrifuge.

The solids that are recovered in the first separator, also soluble in sodium hydroxide, are led to a second separator wherein they are subjected to extraction with the mixture of polar solvents defined above introduced therein by any convenient entry line. Such separation can be carried out at a temperature of about 20° to about 100° C., preferably about 25° to about 50° C., and a pressure of about atmospheric to about 500 pounds per square inch gauge (about atmospheric to about 35 kilograms per square centimeter), preferably about atmospheric to about 100 pounds per square inch gauge (about atmospheric to about 7 kilograms per square centimeter). The mixture of polar solvents used herein to recover the desired acid mixture can be varied over a wide range in any amount sufficient to extract the desired acid mixture from the solid mixture in the first extractor. Thus, the weight ratio of total polar solvent to solid acid mixture can be in the range of about 1:1 to about 10:1, preferably about 2:1 to about 5:1.

The solid material, insoluble in the mixture of solvents, is removed from the second separator by one line and the polar solution of the novel acid mixture by another line. The polar solution is then led to a drier wherein the mixture of polar solvents is separated therefrom by one line and the desired novel polar-soluble, water-insoluble polyaromatic, polycarboxylic acid mixture claimed herein is recovered by another line. As before, the acid mixture in the drier must be treated by so correlating the conditions to remove the mixture of polar solvents therefrom in such manner so as to minimize and, preferably, avoid, decarboxylation and denitrofication. The temperature can be in the range of about 10° to about 100° C., preferably about 20° to about 50° C., the pressure about 10 millimeters of mercury to about atmospheric, preferably about 30 millimeters of mercury to about atmospheric, for about 0.5 to about 24 hours, preferably about one to about five hours.

The filtrate obtained in the first separator is removed therefrom and will contain water, nitric acid and most of the inorganic material (ash) that was present in all the carbonaceous charge. In addition there can also be present other oxidized material, which are primarily organic acids soluble in polar solvents and in water.

DESCRIPTION OF PREFERRED EMBODIMENTS

A North Dakota Lignite analyzing as follows, on a substantially moisture-free basis, was subjected to oxidation using 70 weight percent aqueous nitric acid as the oxidant: 65.03 weight percent carbon, 4.0 weight percent hydrogen, 27.0 weight percent oxygen, 0.92 weight percent sulfur, 0.42 weight percent nitrogen and 0.04 weight percent moisture. The ash was further analyzed and found to contain 43 weight percent oxygen, 7.8 weight percent sulfur and the remainder metals. The weight ratio of lignite to nitric acid (as 100 percent nitric acid) and water in the reactor was 1:1:1. The reaction mixture was stirred and maintained at a temperature of 80° C. and a pressure of 800 pounds per square inch gauge (55 kilograms per square centimeter) for five hours. Nitrogen oxides were permitted to escape from the reaction zone as they evolved.

At the end of the reaction period the product slurry was withdrawn from the reaction zone and filtered to obtain a solids fraction and a filtrate. Portions (100 grams) of the solids fraction were each dissolved in a number of polar solvents with the following results.

TABLE III

| Solvent | Grams | Solubility Data | |
| --- | --- | --- | --- |
| | | Weight Percent Soluble | Weight Percent Insoluble |
| Methanol | 100 | 55.8 | 44.2 |
| Isopropanol | 100 | 51.1 | 48.9 |

TABLE III-continued

| Solvent | Grams | Solubility Data | |
|---|---|---|---|
| | | Weight Percent Soluble | Weight Percent Insoluble |
| Acetone | 100 | 65.0 | 35.0 |
| Methyl Ethyl Ketone | 100 | 39.2 | 60.8 |

Other portions (100 grams) of the solids were dissolved in mixtures of ketones and alcohols, wherein the components thereof were present in an amount sufficient to form an azeotropic mixture, with the following results.

TABLE IV

| Solvent Solution | | | Weight Ratio: Ketone/ Alcohol* | Solubility Data | | | |
|---|---|---|---|---|---|---|---|
| | | | | Weight Percent Soluble | | Weight Percent Insoluble | |
| Total Grams | Ketone | Alcohol | | Found | Expected** | Found | Expected** |
| 100 | Methyl Ethyl Ketone | Isopropyl Alcohol | 68:32 | 83.8 | 43.0 | 16.2 | 57.0 |
| 100 | Acetone | Methyl Alcohol | 88:12 | 75.0 | 63.9 | 25.0 | 36.1 |
| 100 | Methyl Ethyl Ketone | Methyl Alcohol | 30:70 | 87.4 | 50.9 | 12.6 | 49.1 |

*Values taken from "Azeotropic Data", Advances in Chemistry Series, No. 6, published by the American Chemical Society, Washington, D. C., 1951.
**Expected values based on the solubilities obtained from individual polar solvents in Table III.

Comparison of the data obtained in Table IV with that of Table III clearly illustrates the uniqueness of the invention claimed herein. In each case wherein the solvent solution contained both a ketone and an alcohol, unexpectedly larger amounts of polycyclic aromatic polycarboxylic acids were obtained than would have been predicted on the basis of the results obtained with either of the polar solvents alone. An additional advantage is obtained herein because the mixture of polar solvents can form an azeotropic mixture. Thus, when the polar solvent solution containing the desired acid mixture dissolved therein is subjected to drying conditions, as set forth hereinabove, to separate the polar solvents from the desired acid mixture, the solvent mixture will come off cleanly as a single solution which can then be recycled to the second separator defined above for recovery of additional acid mixture. Not only is the separation of solvent solution from the acid mixture thereby facilitated, but since the ratios of components present in the solvent solution will remain constant the amount of acid mixture recovered will also remain constant.

Since the novel mixtures herein have abundant functionality in both carboxyl and nitro groups, it is apparent that the mixtures lend themselves to many known chemical reactions, for example, esterification of the carboxyl groups, hydrogenation of the nitro groups to amines, etc. Thus, the novel mixtures defined herein are effective blowing agents for the purpose of incorporating the same in well-known resins, such as polyethylene, to permanently increase the volume of the resin as shown in application Ser. No. 696,743, of J. G. Schulz and E. T. Sabourin filed June 16, 1976, now U.S. Pat. No. 4,101,469 dated July 18, 1978.

Obviously, many modifications and variations of the invention, as hereinabove set forth, can be made without departing from the spirit and scope thereof and, therefore, only such limitations should be imposed as are indicated in the appended claims.

We claim:

1. In a process for preparing a mixture of polycyclic, aromatic, polycarboxylic acids carrying nuclear nitro groups that is soluble in a mixture consisting essentially of acetone or methyl ethyl ketone and methyl alcohol or isopropyl alcohol but insoluble in water which consists essentially in subjecting a slurry containing coal to reaction with aqueous nitric acid having a concentration of about 5 to about 90 percent at a temperature of about 15° to about 200° C. for about 0.5 to about 15 hours and mechanically separating the solids in the resulting slurry, the improvement which consists essentially in extracting said separated solids with a mixture consisting essentially of acetone or methyl ethyl ketone and methyl alcohol or isopropanol in amounts to form an azeotropic mixture and then separating said ketone and said alcohol from the extract to obtain said mixture of polycyclic, aromatic, polycarboxylic acids.

2. The process of claim 1 wherein the ketone is methyl ethyl ketone.

3. The process of claim 1 wherein the ketone is acetone.

4. The process of claim 1 wherein alcohol is methyl alcohol.

5. The process of claim 1 wherein the alcohol is isopropyl alcohol.

6. The process of claim 1 wherein the nitric acid has a concentration of about 10 to about 70 percent and the reaction is carried out at a temperature of about 50° to about 100° C. for about two to about six hours.

7. The process of claim 1 wherein the mechanical separation is effected by filtration.

8. The process of claim 1 wherein the separation of polar solvents is effected by subjecting the extract to drying.

9. The process of claim 1 wherein the recovered ketone and alcohol are recycled to the extraction stage.

10. The process of claim 1 wherein the coal is lignite.

* * * * *